United States Patent [19]

Hay et al.

[11] Patent Number: 5,011,998
[45] Date of Patent: Apr. 30, 1991

[54] AROMATIC TERTIARY AMINES, ENAMINES, DEOXYBENZOINS AND BENZILS

[76] Inventors: Allan S. Hay, 5015 Glencairn Ave., Montreal, Quebec H3W 2B3; Martino Paventi, 11786 28th Avenue, Montreal, Quebec H1E 9Z7, both of Canada

[21] Appl. No.: 475,992

[22] Filed: Jan. 6, 1990

[51] Int. Cl.⁵ ................... C07C 211/45; C07C 211/55
[52] U.S. Cl. ........................................ 564/384; 564/378
[58] Field of Search ................................ 564/384, 387

[56] References Cited
PUBLICATIONS
Agata et al., Chemical Abstracts, vol. 113 (1990) 31973a.

Primary Examiner—Richard L. Raymond
Attorney, Agent, or Firm—Swabey Ogilvy Renault

[57] ABSTRACT

A novel synthesis of aromatic tertiary amines involves reacting an aromatic anil and an aromatic ether in a molar ratio of 1:1; adjusting the ratio to 2:1 produces novel enamines and by employing a two step process for enamine production, various unsymmetrically substituted enamines can be obtained which are readily hydrolyzed to corresponding deoxybenzoins which in turn are readily oxidized to benzils, the aromatic tertiary amines may be used to produce charge transport layers in xerography, while the benzils may be used to produce a variety of desired polymers.

2 Claims, No Drawings

AROMATIC TERTIARY AMINES, ENAMINES, DEOXYBENZOINS AND BENZILS

BACKGROUND OF THE INVENTION

1. Field of the Invention

This invention relates to novel syntheses of aromatic tertiary amines and aromatic enamines as well as to novel aromatic enamines and the syntheses therefrom of deoxybenzoins and benzils.

2. Description of Prior Art

The "anil" reaction of Scheme 1 developed by Siegrist (A. E. Siegrist et al, Advances in Heterocyclic Chemistry 23, 171 (1978)) has been utilized for the synthesis of a large number of substituted stilbenes (3) by the condensation of an anil (1) with a methyl-containing aromatic compound (2). The aryl groups Ar, Ar' and Ar'' can be hydrocarbon or a wide variety of heterocyclic groups. The reaction:

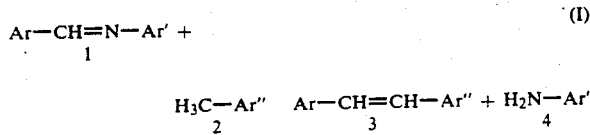

takes place in the presence of strong bases such as potassium tert-butoxide or powdered potassium hydroxide in N,N-dimethylformamide solution at 25°–100° C. and since the aromatic amine (4) is the coproduct in the reaction the strongly basic conditions are maintained in the reaction. The reaction has also been utilized in Scheme 2 for the synthesis of 2-phenylbenzofuran (6) by the intramolecular condensation of the Schiff's

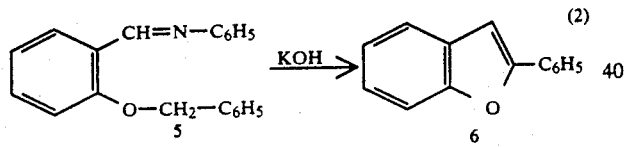

base (5) derived from 1-formyl-2-benzyloxybenzene and aniline, (W. Sahm et al Justus Liebigs Ann. Chem., 523 (1974).

Aromatic tertiary amines have previously been described for the production of charge transport layers in xerography in U.S. Pat. Nos. 4,115,116; 4,047,948; 4,047,949; 4,081,274 and 4,232,103 and polymers containing these amine moieties have been synthesized (U.S. Pat. Nos. 4,806,443 and 4,806,444).

SUMMARY OF THE INVENTION

It is an object of this invention to provide a novel synthesis of aromatic tertiary amines.

It is a further object of this invention to provide aromatic tertiary amines for use in the production of charge transport layers in xerography.

It is a further object of this invention to provide novel syntheses for the production of aromatic enamines.

It is yet another object of this invention to provide a novel synthesis for the production of aromatic enamines from aromatic tertiary amines.

It is still another object of this invention to provide a novel synthesis of aromatic enamines from aromatic anils and aromatic ethers.

It is yet another object of this invention to provide novel aromatic enamines.

It is a still further object of this invention to provide a process for producing deoxybenzoins.

It is yet another object of this invention to provide a process for producing benzils.

In accordance with this invention it has surprisingly been found that reacting an aromatic ether with an aromatic anil in a substantially 1:1 molar ratio produces an aromatic tertiary amine.

In view of the reaction of Scheme 2 referred to hereinbefore such reaction would have been expected to produce an enol ether rather than an aromatic tertiary amine.

It has additionally been found that aromatic enamines are by-products of the reaction, but that when the molar ratio of the anil to the ether is increased to 2:1, the enamine becomes the major product.

The aromatic enamine is readily hydrolysed to a corresponding deoxybenzoin and secondary aromatic amine thereby providing a new synthesis for a wide range of deoxybenzoins.

Deoxybenzoins are readily oxidized to corresponding benzils thereby providing a facile and economically viable synthesis of benzils from readily available starting materials.

DESCRIPTION OF PREFERRED EMBODIMENTS

(i) Aromatic Tertiary Amines

The process of the invention provides for the preparation of aromatic tertiary amines of formula (I):

by reacting an aromatic anil of formula (II) with an aromatic ether of formula (III):

wherein $Ar_1$, $Ar_2$, $Ar_3$ and $Ar_4$ are each aromatic radicals independently selected from:

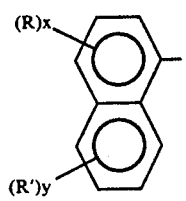

-continued

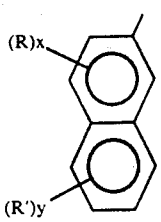

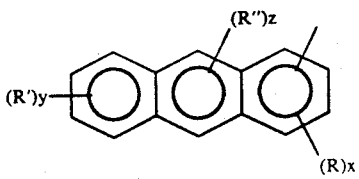

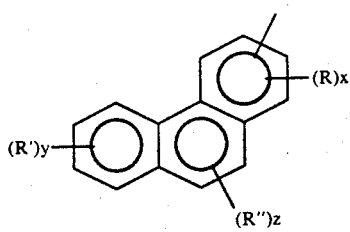

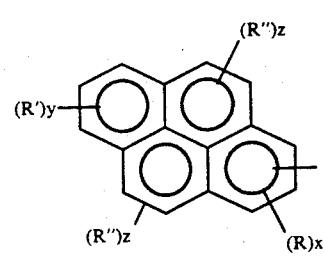

wherein x and y are integers independently selected from 0, 1, 2 or 3, z is an integer independently selected from 0, 1 or 2 and R, R' and R" are each independently selected from halogen atoms selected from fluorine, chlorine and bromine; alkyl of 1 to 6 carbon atoms, alkenyl of 2 to 6 carbon atoms; aryl of 6 to 12 carbon atoms, aralkyl of 7 to 18 carbon atoms; aralkenyl of 8 to 18 carbon atoms; alkoxy of 1 to 6 carbon atoms; thioalkoxy of 1 to 6 carbon atoms; aryloxy of 6 to 12 carbon atoms and thioaryloxy of 6 to 12 carbon atoms.

This process is, in particular, carried out employing a molar ratio of the anil (II) to the ether (III) of 1:1 or about 1:1, at a temperature of 20° to 100° C., in a basic, anhydrous medium.

In particular, the medium suitably comprises a polar, aprotic organic solvent, for example, dimethylformamide, dimethylacetamide or N-methylpyrrolidone, which is rendered strongly basic. In particular, the strong basic character may be achieved by the presence of a strong base, for example, sodium or potassium tert. butoxide, sodium amide or sodium dimethyl amide the latter may optionally be generated in situ from sodium in N,N-dimethylformamide. Mixtures of such bases may be employed.

It has been suggested that the known Wittig rearrangement of benzylphenyl ether of Scheme 3:

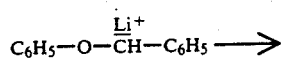

(3)

-continued

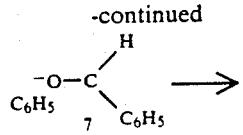

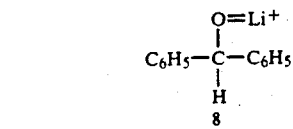

proceeds by a mechanism involving the intermediary of a radial pair 7 including a radical anion, which pair collapses to the alkoxide of the diarylcarbinol 8.

Based on this mechanism, a possible mechanism for the process of this invention is that a similar radical anion undergoes electronic transfer with the aromatic anil to produce an aromatic amine radical anion and an aromatic aldehyde which new radical anion collapses with the aryl radical of the pair according to Scheme 4:

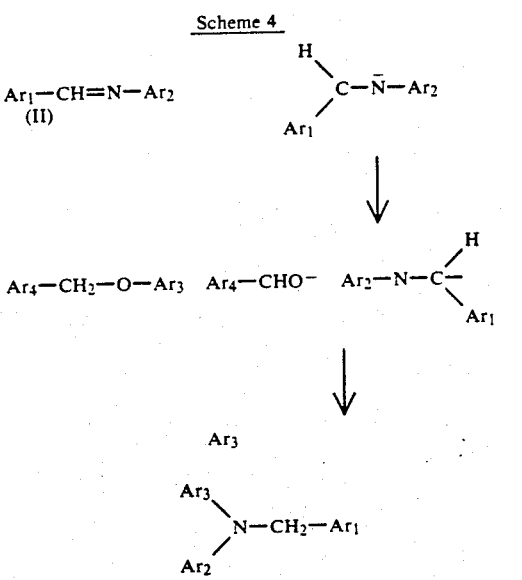

This synthesis of aromatic tertiary amines is much simpler than existing syntheses which require a large number of steps. Additionally it is possible to conveniently produce non-symmetric aromatic tertiary amines by the method of the invention.

The aromatic tertiary amines may be used in the preparation of charge transport layers in xerography, as well as in the production of aromatic enamines in another aspect of the invention.

(ii) Aromatic Enamines

The novel aromatic enamines of this invention may be represented by formula (V):

(V)

and within this class enamines of the formula (IV):

$$\begin{array}{c} Ar_1CH \\ \parallel \\ Ar_1C-N \end{array} \begin{array}{c} Ar_2 \\ \diagdown \\ \diagup \\ Ar_3 \end{array} \quad (IV)$$

in which $Ar_1$, $Ar_2$, $Ar_3$ and $Ar_4$ are as defined previously and $R_5$ is alkyl of 1 to 8 carbon atoms or a radical $Ar_6$, wherein $Ar_6$ is independently selected from the same class of values as set forth for $Ar_1$, $Ar_2$, $Ar_3$ and $Ar_4$.

The enamines (IV) are produced by reacting the previously described aromatic anil (II) and aromatic ether (III) in a molar ration of 2:1 or about 2:1. This reaction is suitably carried out at a temperature of 20° to 100° C. in the presence of a strong base and an anhydrous medium as described above for the preparation of the aromatic tertiary amines (I). In this case both radicals $Ar_1$ are the same.

The broader class of enamines (V) can be produced by reacting an aromatic anil (II) with an aromatic tertiary amine (I) in which case $R_5$ is the radical of formula $Ar_6$, and $R_1$ and $R_4$ can be the same or different; or by reacting the aromatic anil (II) with an aromatic tertiary amine of formula (VII):

$$Ar_4-CH_2-N\begin{array}{c}Alk\\ \diagdown \\ Ar_3\end{array} \quad (VII)$$

in which $Ar_3$ and $Ar_4$ are as defined above and Alk is alkyl of 1 to 7 carbon atoms.

The tertiary amines of formula (VII) may be prepared by known techniques, for example, the benzylation of an N-alkylaniline with a benzyl chloride or benzyl bromide, with appropriate substituents $R_3$ and $R_4$ in the aromatic nuclei of the reactants.

The aromatic tertiary amines (I) may be prepared by the process of the invention or by benzylation of diarylamines with a benzyl chloride or bromide, it being understood that the reactants have the appropriate substituents $R_1$, $R_2$ and $R_3$ in their nuclei.

(iii) Deoxybenxoins

Hydrolysis of the enamines (IV) and (V) produces the corresponding deoxybenzoins (VIII) and (IX) respectively:

$$\begin{array}{cc} Ar_1-CO-CH_2-Ar_1 & Ar_4-CO-CH_2-Ar_1 \\ (VIII) & (IX) \end{array}$$

wherein $Ar_1$ and $Ar_4$ are as defined above.

This hydrolysis proceeds readily under mild acid conditions, for example, by heating under reflux in a solvent such as tertrahydrofuran in the presence of a mineral acid such as hydrochloric acid or sulphuric acid.

A secondary amine of formula (XXI):

$$Ar_3-N\begin{array}{c}R_5\\ \diagdown \\ H\end{array} \quad (XXI)$$

wherein $Ar_3$ and $R_5$ are as defined above, is formed as a by-product of the hydrolysis of the enamine. This secondary amine (XXI) may be benzylated with an aryl halide of formula (XXII):

$$Ar_4-CH_2X \quad (XXII)$$

wherein $Ar_4$ is as defined above and X is Cl or Br, to generate an aromatic tertiary amine of formula (XX):

$$Ar_4-CH_2-N\begin{array}{c}R_5\\ \diagdown \\ Ar_3\end{array} \quad (XX)$$

wherein $Ar_3$, $Ar_4$, and $R_5$ are as defined above; and this tertiary amine (XXIII) may be reacted with an anil of formula (II) as described above, in a molar ratio of at least approximately 1:1, and at a temperature of 20° to 100° C., thereby regenerating the enamine of formula (V).

(iv) Benzils

Oxidation of the deoxybenzoins (VIII) and (IX) produces the corresponding benzils (X) and (XI), respectively:

$$\begin{array}{cc} Ar_1-CO-CO-Ar_1 & Ar_4-CO-CO-Ar_1 \\ (X) & (XI) \end{array}$$

The oxidation of deoxybenzoins to benzils can be carried out by several methods. The most commonly used method utilizes selenium dioxide as the oxidizing agent (for a review see Comprehensive Organic Chemistry, Volume I, pp. 1201-3, Pergamon Press, 1979). More recently, M. B. Floyd, M. T. Du, P. F. Fabio, L. A. Jacob and B. D. Johnson (J. Am. Chem. Soc. 1987, 50, 5022) utilized aqueous hydrobromic acid in diemthyl sulfoxide to oxidize acetophenones and deoxybenzoins to arylglyoxals and benzils, respectively.

These benzils are useful in the synthesis of polyquinoxalines, hindered polyphenyls and highly substituted phthalic anhydrides, which react with diamines to produce polyimides as illustrated in the following:

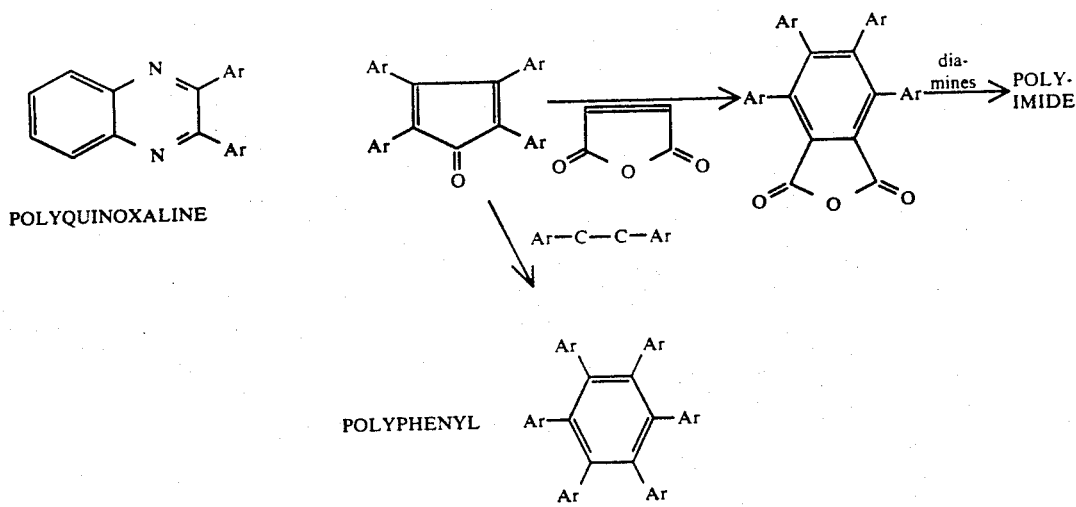

Benzil readily undergoes a condensation reaction with diphenylacetone to yield tetraphenylcyclopentadienone which then will undergo a Diels-Alder reaction with maleic anhydride to give tetraphenylphthalic anhydride. (cf. Organic Synthesis, Coll Vol. 3, pp. 806-808). It is thus feasible to synthesize bis-dianhydrides from the appropriate tetraketone which can then be used as monomers for the synthesis of

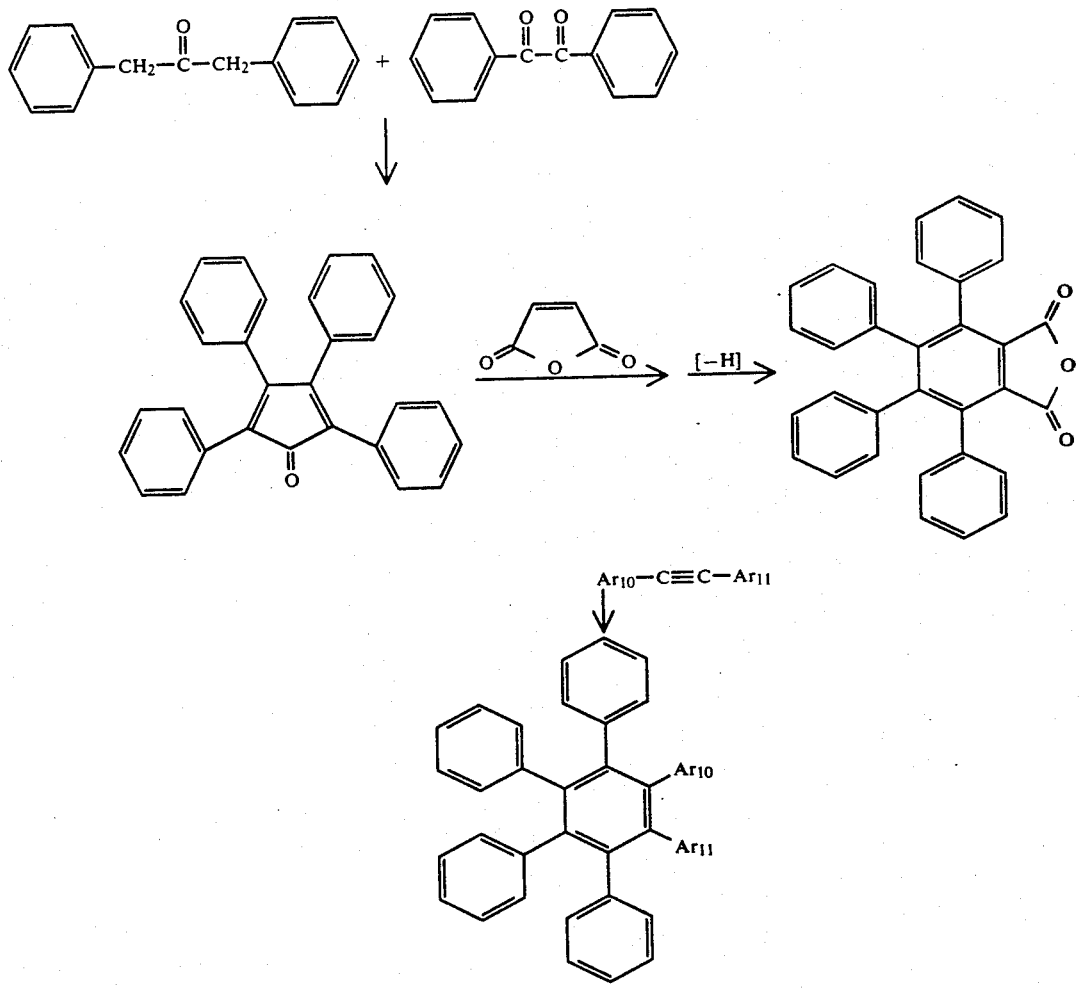

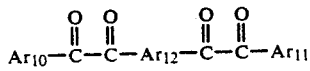 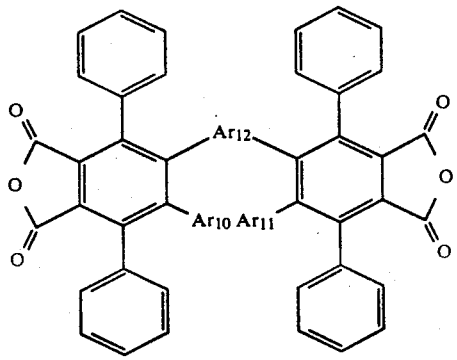

polyimides and other polymers.

Tetraphenylcyclopentadienones also undergo a Diels-Alder reaction with acetylenes (Ar$_{10}$=Ar$_{11}$=H or aryl, Ar$_{12}$=arylene) to give the completely aromatic structure, e.g. reaction with tolan yields hexaphenylbenzene in very high yield. This reaction has also been utilized to synthesize polyphenyls by reaction of the appropriate bis(tetraphenylcyclopentadienone) with bis-acetylene. (J. K. Stille and G. K. Noren J. Pol. Sci., Pol. Lett. Ed. 7, 525, (1969)).

Benzils also condense readily with o-phenylenediamines to give substituted quinoxalines and this reaction has been utilized to synthesize high molecular weight polyquinoxalines by starting with the appropriate tetraketone and tetraamine. (J. K. Stille, U.S. Pat. No. 3,661,850, 1972; W. Wrasidlo and J. M. Augl, Macromolecules 3, 544 (1970)).

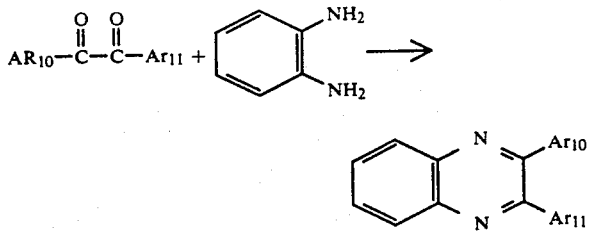

The substituents R, R' and R" may be located in any position of the aromatic radicals Ar$_1$, Ar$_2$, Ar$_3$, Ar$_4$ and Ar$_6$, for example, the o, m or p position, of their respective aromatic nuclei, and such nuclei may be mono- di- or tri-substituted by the values R$_1$, R$_2$, R$_3$, R$_4$ and R$_6$ (other than hydrogen atoms). It will be understood that in the case of di- or tri-substitution the R, R' and R" substituents may be the same or different.

The invention is further illustrated in particular and preferred embodiments by reference to the following examples.

EXAMPLES

Experimental

General procedure for the preparation of the sodium/-dimethylformamide (Na/DMF) mixture To dimethylformamide (40 of 50 ml) was added sodium (1.0 g, 0.043 mol) in seven portions at 105°-110° C. under a slow stream of nitrogen and with stirring. Additional portions of sodium were introduced after the initial vigorous reaction had abated. The mixture was brought to the desired temperature and the substrates were added using the remaining volume of dimethylformamide to dissolve them.

General procedure for the preparation of Anils: N-(Phenylmethyl)benzeneamine

Benzaldehyde (31.84 g, 0.300 mol) and aniline (27.94 g, 0.300 mol) in benzene (100 ml) were heated to remove the water using a Dean-Stark trap. After 5.4 ml of water had been collected, the benzene was stripped off and the residual oil poured into a beaker. On treating with petroleum ether (10-20 ml) the oil crystallized. This mass was suction filtered and washed with some additional petroleum ether. Recrystallization from hexane gave off-white needles.

General Procedure for preparing the arylbenzyl ethers

The arylphenoxide (anhydrous, 0.30 mol) and an equivalent amount of benzylchloride were heated to 80° C. for 1.5 hr in dimethylformamide (100 ml). The ether was precipitated by addition of water, 300 ml, filtered and dried. This product was usually pure enough for the next reaction. Recrystallization from ethanol, 95%, gave the pure benzyl ethers.

4,4'-Bis(benzyloxy)1,1'-biphenyl

This diether is produced in one step using the same procedure above (methanolic KOH was used) in >90% yield, mp 222°-224° C. from benzene. FTIR (KBr wafer)γ:3092, 3064, 3048, 3034, 2939, 2906, 2864, 1608, 1508, 1500, 1469, 1455 cm$^{-1}$; MS [m/e (70 eV, % of base peak)] (PhCH$_2$O)$_2$(C$_6$H$_4$—C$_6$H$_4$) 366 (M$^+$·, 25.9), 275 (M$^+$—PhCH$_2$·, 15.8),91 (PhCH$_2$$^+$·, 100).

EXAMPLE 1

N,N-Diphenylbenzenemethanamine

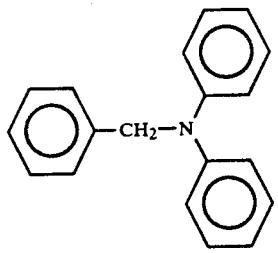

N-phenylbenzaldimine (1.81 g, 0.010 mol) and benzylphenyl ether (1.84 g, 0.010 mol) were heated at 75° C. in Na/DMF solution (2.0 g: 50 mL) for 30 minutes. The solution was then poured in 200 mL of water, the precipitate was filtered washed with water and dried. Recrystallization from methanol, 70 mL, gave white needles (73% isolated) mp 88°-90° C. (lit mp 86-7° C.[8], 88-9° C.9). No depression in melting point occurred when this material was admixed with an authentic sample prepared from diphenylamine and benzyl chloride. Byproducts in the preparation of N,N-diphenylbenzene-methanamine reaction at 100° C.

The mother liquors from the recrystallization of N,N-diphenylbenzenemethanamine were combined with the petroleum ether extracts 3×150 mL of the aqueous dimethyl formamide filtrate. The organics were evaporated and the residual oil chromatographed on 25 g of silica. The first eluent was petroleum ether giving one major fractional mixture containing some more benzyldiphenylamine. Other fractions crystallized some material mp 203-4° C. (m/e=181) which was not characterized further. The later fractions contained some material mp 168-70° C. from methanol. A mass spectrum of this last compound appears consistent with m/e=197 for N-phenylbenzamide.

The initial aqueous dimethylformamide solution was extracted with chloroform 3×150 mL. The solvent was evaporated and the residual oil was chromatographed on 30 g of silica with ethyl acetate/petroleum ether 1:1. The last fractions upon concentration and cooling slowly crystallized some material which was washed with ether and crystallized from the same mp 134-7° C. as colorless needles. The spectra are consistent with the literature for N,N-dimethyl-N'-phenylurea mp 132-3° C. and 131-2° C. The middle fraction was chromatographed on 60 g of silica using the same eluent to give a small amount of N,N-dimethyl-α-(phenylamino)benzeneacetamide (see above). Also an impure oil was characterized by comparing the FTIR and mass-spectrum-fragmentation pattern of an Aldrich sample of N,N-dimethylbenzamide. Only in the infrared spectrum there was evidence, from N-H and C=O stretching bands, that at least another product was contaminating the N,N-dimethylbenzamide.

EXAMPLE 2

N,N-Diphenyl-1-naphthalenemethanamine

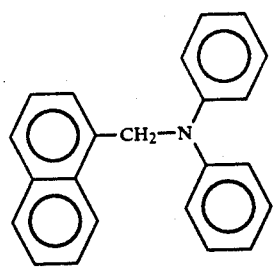

N-phenylnaphthaldimine (2.20 g, 0.010 mol) and benzylphenyl ether (1.84 g, 0.010 mol) were reacted as above for the preparation of benzyldiphenylamine. Aqueous work-up afforded a precipitate which was isolated by filtration and recrystallized from 95% ethanol to yield 2.3 g (74%) of needles, mp 170°-172° C. Anal. calcd. for $C_{23}H_{19}N$: C 89.28, H 6.19, N 4.53%; found C 89.11, H 6.26, N 4.44%. $^1H$ NMR (200 MHz, CDCl$_3$)δ (assignment): 5.52 (s, 2H, CH$_2$), 7.00-8.10 (m, 17H, aromatic). MS [m/e (70 ev, % of base peak)] $(C_{10}H_7)CH_2N(C_6H_5)_2$ 309 (M+·, 4.8), 308 (M+−H., 29.0), 168 (M+−((C$_{10}$H$_7$)CH$_2$)., 18.0), 141 ((C$_{10}$H$_7$)CH$_2$)+·, 100). FTIR (CDCl$_3$): 3063, 3040, 1606, 1602, 1594, 1584, 1574, 1559, 1512, 1501, 1497, 1488, 1485, 1474, 1465, 1460, 1451 cm$^{-1}$.

EXAMPLE 3

N-(4-Methoxyphenyl)-N-phenyl-1-naphthalenemethanamine

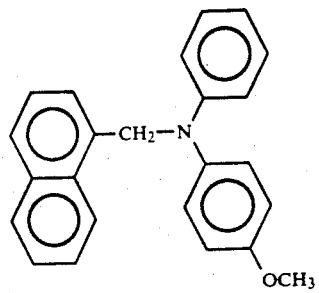

N-phenylnaphthldimine (2.20 g, 0.010 mol) and benzyl-4-methoxyphenyl ether (2.14 g, 0.010 mol) were reacted in Na/DMF solution (50 mL) at 100° C. for 30 min. A similar work-up as for the preparation of benzyldiphenylamine gave 0.50 g. of product (15%) which after recrystallization from hexane had mp 154°-159° C. $^1H$ NMR (200 MHz, CDCl$_3$) δ (assignment): 3.79 (d, J=1.40 Hz, 3H, OCH$_3$), 5.39 (s, 2H, CH$_2$), 6.78-6.89 (m, 5H, aromatic), 7.16-8.07 (m, 11H, aromatic). MS [m/e (70 eV, % of base peak)] $(C_{10}H_7)CH_2N(C_6H_5(CH_3O(C_6H_4))$ 339 (M+·, 23.0), 198 (M+−((C$_{10}$H$_7$)CH$_2$)., 58.3), 141 ((C$_{10}$H$_7$)CH$_2$)+·, 100). Analysis: Calcd. for $C_{24}H_{21}NO$: C 84.92, H 6.24, N 4.13%; found (average of two runs); C 85.06, H 6.61, N 3.99%.

EXAMPLE 4

Bis[4-(N,N-diphenylaminomethyl)phenoxy]methane

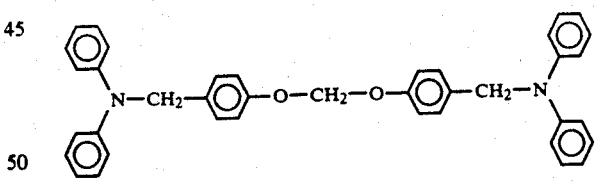

Di(N-phenylcarboxaldimine-4-phenoxy) methane (2.03 g, 0.0050 mol) and benzylphenyl ether (1.84 g, 0.010 mol) were heated in Na/DMF solution (50 ml) at 100° C. for one hour. Similar work-up as for the preparation of benzyldiphenylamine, double chromatography on silica using carbon tetrachloride as eluent gave 0.40 g (14%) of the title compound, mp 99°-100° C. from hexane. Analysis calcd. for $C_{39}H_{34}N_2O_2$: C 83.24, H 6.09, N 4.98%; found: C 83.44, H 6.14, N 4.96%, $^1H$ NMR (200 MHz, CDCl$_3$)δ (assignment): 4.96 (s, 4H, CH$_2$N), 5.67 (s, 2H, OCH$_2$O), 6.90-7.09 (m, 16H, aromatic), 7.20-7.30 (m, 12H, aromatic). FTIR (CDCl$_3$): 3098, 3075, 3045, 1604, 1591, 1575, 1507, 1498 cm$^{-1}$.

EXAMPLE 5

N-[4-(1,1-dimethylethyl)phenyl-naphthalenemethanamine

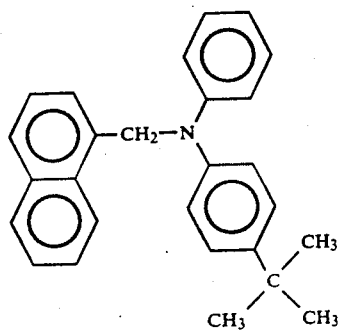

N-phenylnaphthaldimine (2.20 g, 0.010 mol) and benzyl-t-butylphenylether (0.01 mol) were reacted in Na/DMF solution (50 ml) at 100° C. for 30 min. The usual work-up followed by chromatography on silica using petroleum ether/chloroform 4:1 as eluent gave, after crystallization from petroleum ether/methanol, 1.3 g (36%) of the title compound, mp 135°–137° C. as prisms. Anal. calcd. for $C_{27}H_{27}N$: C 88.72, H 7.44, N 3.83%: found: C 88.50, H 7.49, N 3.76%. $^1$H NMR (200 MHz, $CDCl_3$)δ (assignment): 1.29 (d, J=1.20 Hz, 9H, $C(CH_3)_3$), 5.45 (s, 2H, $CH_2N$), 6.86–8.04 (m, 16H, aromatic). MS [m/e (70 eV, % of base peak)] $(C_{10}H_7)CH_2N(C_6H_5)((C_6H_4)C(CH_3)_3)$ 365 ($M^+$·18.9), 350 ($M^+$—$CH_3$·, 10.6), 141 ($C_{10}H_7CH_2^+$·, 100). FTIR ($CDCl_3$)ν: 3063, 3040, 2966, 2904, 2870, 1596, 1515, 1512, 1500, 1496, 1477, 1459 $cm^{-1}$.

EXAMPLE 6

N-(1-naphthyl)-N-phenyl-naphthalenemethanamine

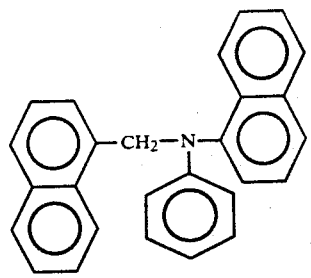

(1-Naphthylmethoxy)-1-naphthalene (2.84 g, 0.010 mol) and N-phenylnaphthaldimine (2.20 g, 0.010 mol) were reacted in Na/DMF (1 g, 50 mL) at 75° C. for 30 min. Aqueous work-up afforded a sticky precipitate which was dissolved in ether treated with 7.0 g of silica and the ether was evaporated. This dry silica was added to a bed of ~40 g of silica wetted with petroleum ether-/ethyl acetate 98:2 and eluted with the same solvent. The fractions containing the title compound were combined. After evaporation of the solvent the residue was recrystallized from ethyl acetate mp 179–80° C. (65% based on a calibration graph). $^1$H NMR (200 MHz, $CDCl_3$)δ (assignment): 5.47 (s, 2H, $NCH_2Ph$), 6.56–6.77 (m, 3H, aromatic). MS [m/e (70 eV, % of base peak)] $C_{10}H_7CH_2N(C_{10}H_7)(Ph)$ 359 ($M^+$·, 31.6), 218 $((C_{10}H_7NPh)^+$, 31.2), 141 ($C_{10}H_7N^+$, 100); HRMS (m/z) for $C_{27}H_{21}N$ ($M^+$·) calcd. 359.167 found 359.183.

FTIR ($CDCl_3$): 3061, 2890, 2852, 1599, 1575, 1499, 1470, 1398 $cm^{-1}$.

EXAMPLE 7

N,N'-Diphenyl-N,N'-bis(phenylmethyl)[1,1'-biphenyl]-4,4'-diamine

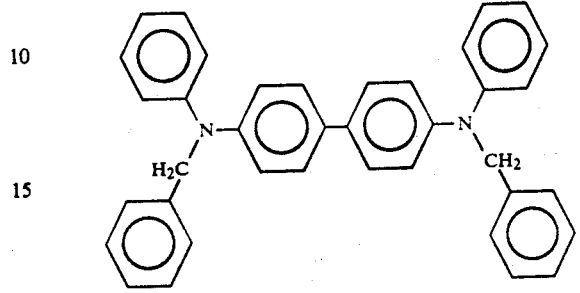

N-Phenylmethylene)benzenamine (3.62 g, 0.020 mol) and 4,4'-bis(phenylmethoxy)[1,1'-biphenyl] (3.66 g, 0.010 mol) were heated in Na/DMF solution (50 mL) at 100° C. for 1 hr. High pressure liquid chromatography indicated a complex mixture from which three products: I (14%), II (10%), and III (8%), were isolated and identified as follows. The Na/DMF mixture was poured into water (100 ml) and extracted with chloroform (3×100 mL). After drying over sodium sulfate, the organic phase was evaporated under reduced pressure. The resulting oil was chromatographed on silica (60 g) using petroleum ether/chloroform 4:1 as eluent separating pure I and a mixture of II and III. Compound I had mp 89°–91° C. from petroleum ether/methanol which was not depressed with an admixture of N,N-diphenylbenzenemethanamine and showed an identical mass-spectrum-fragmentation pattern of this amine. The mixture of II and III was chromatographed on silica (60 g) with the same eluent above to give the separated materials.

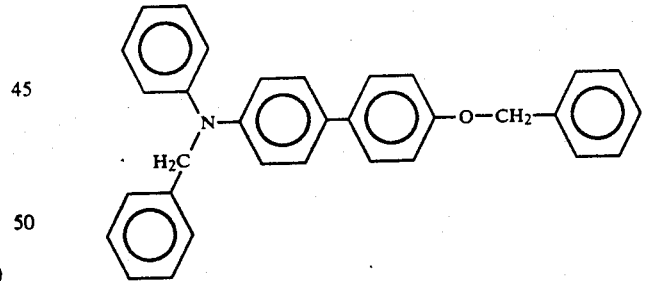

Compound II, the less polar, was recrystallized from ethyl acetate/methanol mp 136°–137° C. Its mass spectra are consistent with the title compound: MS [m/e (70 eV, % of base peak)] $[PhCH_2(Ph)N]_2$ $(C_6H_4—C_6H_4)$ 516 ($M^+$·, 96.2), 425 ($M^+$—$PhCH_2$·, 100), 334 ($M^+$—$2PhCH_2$·, 56.7), 91 ($PhCH_2^+$·, 61.7); (m/2) for $C_{38}H_{32}N_2(M^+)$, calcd. 516.256, found 516.27. Analysis calcd. for $C_{38}H_{32}N_2$: C 88.33, H 6.24, N 5.42%; found (average of two runs): C 88.30, H 6.61, N 5.40%. HRMS FTIR (KBr wafer)γ. 3084, 3058, 3051, 3048, 3031, 3006, 1593, 1508, 1499, 1497, 1450 $cm^{-1}$. Compound III above was crystallized from chloroform/methanol and had a wide decomposition range: 137°–150° C. Its mass spectra are consistent with 4'-(Phenylmethoxy)-N-phenyl-N-(phenylmethyl)[1,1'-biphenyl]-4- amine: MS [m/e (70 eV, % of base peak)] PhCH₂O(C₆H₄—C₆H₄)N(Ph)CH₂Ph 441 (M⁺·, 23.3), 350 (M⁺—PhCH₂·, 39.4), 91 (PhCH₂⁺·, 100); HRMS (m/2) for C₃₂H₂₇NO: calcd. 441.209, found 441.222.

EXAMPLE 8

N-(4-methylphenyl)-N-phenyl-benzenemethanamine

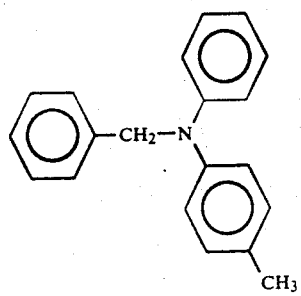

Methyl-4-(phenylmethoxy)benzene (1.98 g, 0.01 mol) and N-(phenylmethylene)benzenamine (1.81 g, 0.01 mol) were reacted in Na/DMF (1 g: 50 mL) at 75° C. for 30 min. Aqueous work-up, extraction with petroleum ether, 3×100 mL, and chromatography with petroleum ether/ethyl acetate 95:5 afforded a total of 1 g. of solid which by HPLC chromatography contained N,N-diphenyl-benzenemethanamine and the title compound in the ratio (6:94 (51% yield by HPLC). The purer fractions from chromatography on silica were combined and the solvent removed. The residual oil was dissolved in methanol and some petroleum ether. On cooling this crystallized the title compound. Two recrystallizations from methanol gave the title compound (98.1% pure; 36% yield), mp 85–6° C. ¹H NMR (200 MHz, CDCl₃)δ (assignment): 2.29 (s, 3H, methyl), 4.97 (s, 2H, —NCH₂Ph), 6.80–6.97 (m, 3H, aromatic) 7.06–7.27 (d, 4H, J=1.37 Hz, —NC₆H₄CH₃), 7.14–7.36 (m, 7H, aromatic). MS [m/e (70 eV, % of base peak)] PhCH₂N(Ph)(C₆H₄)CH₃ 273 (M⁺·, 96.5), 196 (M⁺—Ph·, 31.7), 182 (M⁺—PhCH₃·, 100), 167 (M⁺—PhCH₂—CH₃·, 81.2), 91 (C₇H₇⁺, 98.3). FTIR (CDCl₃): 3089, 3064, 3030, 2924, 2864, 1596, 1572, 1512, 1497, 1453 cm⁻¹.

EXAMPLE 9

N-(2-methylphenyl)-N-phenyl-benzenemethanamine

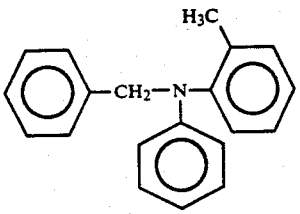

Methyl-2-phenylmethoxybenzene (1.98 g, 0.010 mol) and N-phenylmethylene)benzeneamine (1.81 g, 0.010 mol) were reacted in Na/DMF (1 g: 50 mL) at 75° C. for 30 min. Aqueous work-up, extraction with petroleum ether, 3×100 mL, and evaporation of the solvent gave a solid residue. This material was treated with a little ether to leave a white crystalline compound (36% yield) which was recrystallized from methanol to give the title compound mp 101–2° C. ¹H NMR (200 MHz, CDCl₃)δ (assignment): 2.15 (s, 3H, methyl), 4.84 (s, 2H, PhCH₂N), 6.50–6.56 (m, 2H, aromatic), 6.66–6.77 (m, 1H, aromatic), 7.07–7.42 (m, 11H, aromatic). MS [m/e (70 eV, %. of base peak)] PhCH₂N(Ph)C₆H₄CH₃ 273 (M⁺·, 100), 182 (M⁺ 13 PhCH₃⁺·, 74.1), 180 (PhCNPh)⁺, 55.4), 91 (C₇H₇⁺, 75.4), 77 (Ph⁺·, 48.4); HRMS (m/z) for C₂₀H₁₉N (M⁺·), calcd. 273.152, found 273.1. FTIR (CDCl₃): 3088, 3065, 3028, 2980, 2953, 2928, 2889, 2852, 1598, 1530, 1497, 1455, 1441, 1375, 1348, 1297, 1258, 1231 cm⁻¹. Analysis: Calcd. for C₂₀H₁₉N: C 87.87 H 7.00, N 5.12%; found (average of two runs); C 87.85, H 7.23, N 5.05%.

EXAMPLE 10

N-(4-Chlorophenyl)-N-phenyl-benzenemethanamine

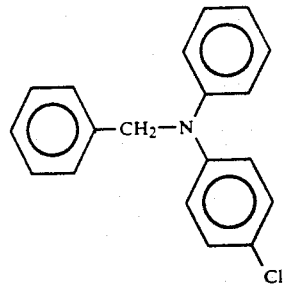

Chloro-4-(phenylmethoxy)benzene (2.18 g, 0.010 mol) and N-(phenylmethylene)benzenamine (1.81 g, 0.010 mol) were reacted in Na/DMF (1 g: 50 mL) at 50° C. for 7 hrs. The reaction was followed by HPLC to about 90% conversion. This technique indicated among other things the presence of the title compound, benzyldiphenylamine, and some unknown material in a ratio 65:18:17. Similar aqueous workup as for the preparation of benzyldiphenylamine and chromatography on silica gave 0.50 g of the title compound mp 94–5° C. from methanol (lit mp 97–7.5° C. 70% yield. This material is contaminated with a small amount of diphenylbenzylamine. ¹H NMR (200 MHz, CDCl₃)δ (assignment): 5.03 (s, 2H, Ph₂NCH₂Ph), 6.96–7.38 (m, 14H, aromatic). MS [m/e (70 eV, % of base peak)] C₁₉H₁₆ClN 293 (M⁺·, 52.8), 295 (M⁺·+2, 28.8), 202 (M⁺—C₇H₇⁺, 22), 167 (C₆H₄NPh)⁺·, 48.3), 91 (C₇H₇⁺, 100). FTIR (CDCl₃): 3066, 3033, 1589, 1494, 1454 cm⁻¹.

EXAMPLE 11

N-(4-Bromophenyl)-N-phenyl-benzenemethanamine

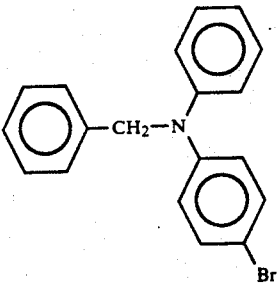

Bromo-4-(phenylmethoxy)benzene (2.63 g, 0.010 mol) and N-(phenyl- methylene)benzeneamine (1.81 g, 0.010 mol) were dissolved in Na/DMF (1 g: 50 mL) and heated at 50° C. for 145 min. Two other reactions were run on the same molar ratios at 100° C. for 15 min and at 30° C. for 24 hrs. The reactions were monitored by HPLC. After the stated periods the title compound and benzyldiphenylamine were produced in the following ratios: at 100° C. 31:69, at 50° C. 77:33, and at 30° C. 94:6. The conversion decreased with temperature: at 100° C. ~100%, at 50° C. ~95%, at 30° C. ~50%. Aqueous workup of the reaction run at 30° C. and chromatography on silica obtained the title compound (98% pure; 77% yield)), mp 97-8° C. from petroleum ether/methanol. $^1$H NMR (200 MHz, CDCl$_3$)δ (assignment): 4.96 (s, 2H,—NCH$_2$Ph), 6.83-6.88 (m, 2H, aromatic), 7.01-7.32 (m, 12H, aromatic). MS [m/e (70 eV, % of base peak)] Ph(BrC$_6$H$_4$)NCH$_2$Ph 337 (M$^+$·, 45.4), 339 (M$^+$·+46.3), 167 (M$^+$·—PhCH$_2$·—Br·, 42.5), 91 (C$_7$H$_7^+$, 100). FTIR (CDCl$_3$): 3089, 3066, 3033, 2919, 2868, 1601, 1584, 1499, 1493, 1487, 1453 cm$^{-1}$.

EXAMPLE 12

Bis[4-(N-phenylmethylamino))phenyl]-2,2-propane

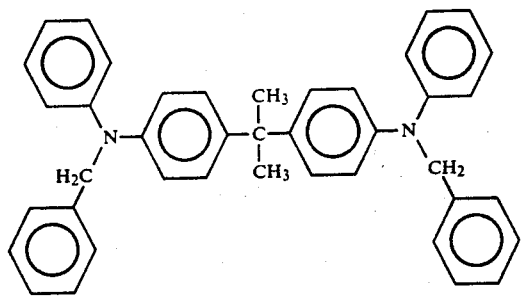

Bis[4-(phenylmethoxy)phenyl]-2,2-propane (2.04 g, 0.005 mol) and N-(phenylmethylene)benzenamine (3.62 g, 0.020 mol) were heated at 75° C. for 5 hrs in Na/DMF (1 g: 50 mL). After this period it was estimated from HPLC that the ratio of N-(phenylmethylene)benzenamine, N,N-diphenylbenzenemethanamine, 2-[4-(N-phenyl-(phenylmethylamino))phenyl]-2-[4-(phenylmethoxy)phenyl]propane (not isolated), the title compound, and an unknown substance (with longer retention time) to be 0.006, 0.0014, 0.0004, 0.003, 0.0006 mol respectively. Aqueous workup precipitated a very viscous oil from which the liquid was decanted and the oil washed with water and methanol successively. This oil was dissolved in diethyl ether and poured onto 10 g of silica, the ether was evaporated off while stirring the mixture. The dried silica with adsorbed material was added to 50 g bed of silica wetted and packed with petroleum ether/benzene 98:2 as the eluent and the material was chromatographed. The purer fractions containing the title compound were chromatographed once more. The cleaner fractions containing the title compound and the unknown 90:10 crystallized on cooling a low melting solid, mp 45°-50° C. (60% yield). MS [m/e (70 eV, % of base peak)] (PhCH$_2$(Ph)NC$_6$H$_4$)$_2$C$_3$H$_6$ 558 (M$^+$·, 90), 543 (M$^+$·—CH$_3$·, 100), 468 (M$^+$·—PhCH$_2$·, 30.9), 452 (M$^+$·—CH$_3$·—PhCH$_2$·—H·, 31.1), 194 (PhNC$_7$H$_6$CH$_3^+$·, 27.7), 91 (C$_7$H$_7^+$, 50.5). FTIR (CDCl$_3$): 3088, 3064, 3033, 2971, 2938, 2872, 1595, 1510, 1497, 1453 cm$^{-1}$.

EXAMPLE 13

N,N'-Diphenyl-N,N'-bis(phenylmethyl)benzene-1,4-diamine

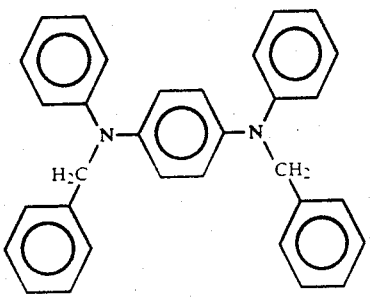

N,N'-Bis(phenylmethylene)benzene-1,4-diamine (1.42 g, 0.005 mol) and phenylmethoxybenzene (1.84 g, 0.010 mol) were heated in Na/DMF (1 g: 50 mL) at 100° C. for 1 hr. Similar workup as for the preparation of benzyldiphenylamine and chromatography on silica using petroleum ether/chloroform 4:1 as eluent gave 0.35 g (16%) mp 149-51° C. from ethyl acetate. $^1$H NMR (200 MHz, CDCl$_3$)δ (assignment): 4.96 (s,4H, PhCH$_2$N—), 6.80-6.97 (m, 6H, aromatic), 7.05 (s, 4H, (PhCH$_2$(Ph)N)$_2$C$_6$H$_4$), 7.16-7.33 (m, 14H, aromatic). MS [m/e (70 eV, % of base peak)] (PhCH$_2$(Ph)N)$_2$C$_6$H$_4$ 440 (M$^+$·, 25.4), 349 (M$^+$·—C$_7$H$_7$·, 24.5), 91 (C$_7$H$_7^+$, 100). HRMS (m/z) for C$_{32}$H$_{28}$N$_2$ (M$^+$·) calcd. 440.225, found 440.227.

EXAMPLE 14

(E)-1-(diphenylamino)-1-phenyl-2-phenylethylene

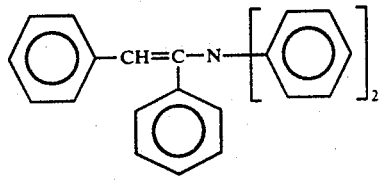

Diphenylbenzylamine (3.92 g, 0.0151 mol) and N-phenylbenzaldimine (3.0 g, 0.0165 nol) were heated for 150 min in dimethylformamide at 75° C., 50 mL, in the presence of potassium tert-butoxide (5.6 g, 0.050 mol). Based on reversed phase HPLC results, after 150 min the conversion was 94% (i.e. ~6% of diphenylbenzylamine was unreacted). From a calibration graph the yield of the title compound was 75%. This material is isolated by pouring the organic solution into water. 150 mL. and filtering the precipitate. The sticky solid was treated with activated charcoal in boiling methanol filtered and cooled. The enamine crystallized slowly as a pale green-yellow prisms mp 87-7° C. $^1$H NMR (200 MHz, CDCl$_3$) δ (assignment): 6.71 (s, 1 H, =CHPh), 6.77-6.85 (m, 2 H, aromatic), 7.05-7.38 (m, 16 H, aromatic) 7.56-7.62 (m, 2 H, aromatic). MS [m/e (70 eV, % of base peak)]Ph$_2$NC(Ph)CHPh 347 (M$^+$·, 46.1), 180 (PhCNPh$^+$, 100), 77 (Ph$^+$, 29.7); HRMS (m/z) for C$_{26}$H$_{21}$N (M$^+$·), calcd. 347.192, found 347.180. FTIR (CDCl$_3$): 3081, 3028, 1590, 1491, 1448 cm$^{-1}$. This material was further identified by hydrolysis (see below). Analysis: calcd. for C$_{26}$H$_{21}$N: C 89.89 H 6.09, N 4.03%; found (average of two runs): C 90.08; H 6.41, N 3.93%.

EXAMPLE 15

Diphenylbenzylamine (1.30 g, 0.0050 mol) and N-phenylbenzaldimine (3.0 g, 0.0165 mol) were heated at 75° C. for 17 h in the base system tBuOH/DMF/Na 1.4 g: 50 mL: 1.4 g: 50 mL: 1.0 g, which was prepared in situ from t-BuOH (1.4 g, 0.020 mol) DMF (25 mL) and sodium metal (1.0 g, 0.043 mol) at 100°–110° C. (similar to the preparation of Na/DMF above). The enamine was formed to about 54% of theory (from a calibration curve) based on diphenylbenzylamine.

EXAMPLE 16

Hydrolysis of (E)-1-diphenylamino-1-phenyl-2-phenylethylene to Deoxybenzoin (E)-1-(Diphenylamino)-1-phenyl-2-phenylethylene (1.0 g, 0.0029 mol) was dissolved in tetrahydrofuran 30 mL and 1.2M hydrochloric acid, 7.0 mL. On heating this solution two phases separated which disappeared on cooling. The progress of the reaction was monitored by reversed-phase HPLC giving the disappearance of reactant and the appearance of products (only one signal appeared for the products). At the end of the hydrolysis, the solution was neutralized by adding an excess of solid sodium bicarbonate, filtered and evaporated. The residue was chromatography on silica using petroleum ether/benzene/ethyl acetate, 90:9:1, as eluent separating firstly diphenyl amine, mp 52–3° C., from petroleum ether and then deoxybenzoin, mp 55–6° C. (lit. 55–6° C., 56° C.), from petroleum ether. Their structures were confirmed by comparison of spectra of the authentic materials.

EXAMPLE 17

Oxidation of Deoxybenzoin to Benzil

To deoxybenzoin (4.91 g, 0.025 mol) dissolved in DMSO (42 mL) at 55° C. was added HBr (48% aqueous, 8.5 mL, 0.075 mol of HBr) and this solution was stirred overnight at 55° C. The solution was poured onto ice-water (300 mL) and cooled for 24 h. The precipitate was filtered, dried and weighted: 4.28 g (76%) mp 90°–94° C. Recrystallization from ethanol gave 3.30 g (63%) of the title compound mp 95–6° C.

EXAMPLE 18

1-(diphenylamino)-1-phenyl-2-(1-naphthyl)ethylene

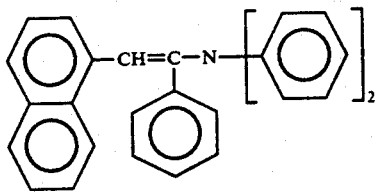

This compound was synthesized from diphenylbenzylamine and N-phenyl-1-naphthaldimine under the same conditions outlined for (E)-1-(diphenylamino)-1-phenyl-2-phenylethylene above. Recrystallizatiom from ethyl acetate/methanol gave small crystals mp 170–2° C. $^1$H NMR (200 MHz, CDCl$_3$) δ (assignment): 6.60–6.90 (m, 2 H, aromatic), 6.80–7.38 (m, 15 H, aromatic), 7.52–7.85 (m, 6 H, aromatic). MS [m/e (70 eV, % of base peak] C$_{10}$H$_7$CHCPhNPh$_2$ 397 (M$^+$, 43.1), 180 (PhCNPh$^+$, 100), 77 (Ph$^+$, 43.2); HRMS (m/z) for C$_{30}$H$_{23}$N (M$^+\cdot$), calcd. 397.183 found 397.195.

EXAMPLE 19

Hydrolysis of (E)-1-(diphenylamino)-1-phenyl-2-(1-naphthyl)ethylene to 2-(1-Naphthyl)-1-phenylethanone

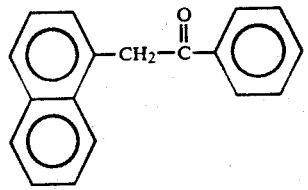

Refluxing (E)-N,N-diphenyl-1-phenyl-2-(1-naphthyl)ethyleneamine (impure see above) in tetrahydrofuran, 30 mL, and 1.9N H$_2$SO$_4$, 3.0 mL, for two hours and aqueous work-up as above gave a mixture of compounds. The enamine was fully hydrolysed as indicated by reversed phase HPLC. Column chromatography on silica 60 using petroleum ether/benzene/chloroform 80:14:6 separated two fractions. The first contained N,N-diphenylbenzylmethanamine (unreacted) and N,N-diphenyl-(1-naphthalene)methanamine. The latter compound was separated pure by fractional crystallization from methanol mp 173–5° C.: admixed with an authentic sample mp 173–3° C. (Example 2) The second fraction contained diphenylamine and was discarded. The third fraction was eluted by adding chloroform to the column. After evaporation of solvent, recrystallization from methanol gave the title compound as white plates mp 109–10° C. (lit 106.5°–107° C., 109°–110° C.). FTIR (CDCl$_3$): 3085, 3067, 3011, 2907, 1692(lit 1675 (C=O, KBr)), 1598, 1581, 1511, 1448, 1417, 1399, 1330, 1275 cm$^{-1}$.

EXAMPLE 20

(E)-1-(diphenylamino)-1-phenyl-2-phenylethylene from Benzylphenyl Ether and N-Phenylbenzaldimine Benzylphenyl Ether (1.84 g, 0.01 mol) and N-phenylbenzaldimine (4:34 g, 0.024 mol) were heated at 75° C. for 2 hours in dimethylformamide, 50 mL, in the presence of potassium tert-butoxide (5.6 g, 0.050 mol). After this period the N-phenylbenzaldimine had decreased to about 10% of the original amount and a 39% yield of the title compound was present according to high pressure liquid chromatography using a calibration graph. After 17.8 hours the yield had increased to 44%.

EXAMPLE 21

(E)-9-(1,2-diphenylethenyl)carbazole

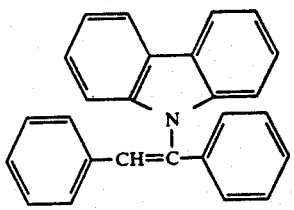

N-Phenylbenzaldimine (1.35 g, 0.0075 mol) and 9-benzylcarbazole (1.29 g, 0.0077 mol) were heated at 75° C. for 30 min in dimethylformamide (dry), 50 mL, and potassium tert-butoxide (0.10 g, 0.00089 mol). Based on reversed-phase HPLC results, the reaction was complete after 3 min. Aqueous work-up as above and recrystallization of the precipitate from methanol gave needles mp 160-2° C. (81%). $^1$H NMR (200 MHz, CDCl$_3$) δ (assignment): 6.85-7.09 (m, 2 H, aromatic). MS [m/e (70 eV, % of base peak)] C$_{26}$H$_{19}$N 345 (M$^+$·, 100), 267 (M$^+$·—PhH, 25.8), 178 PhCCPh$^+$·, 47.5), 167 (carbazole$^+$·, 63.6). HRMS (m/z) for C$_{26}$H$_{19}$N (M$^+$·) calcd. 345.1517 found 345.1513. FTIR (CDCl$_3$): 3083, 3064, 3027, 1624, 1598, 1493, 1479, 1450, 1384, 1335, 1314, 1232 cm$^{-1}$. Analysis: calcd. for C$_{26}$H$_{19}$N: C 90.40, H 5.54, N 4.05%; found: C 90.25, H 5.66, N 4.20%.

EXAMPLE 22

(E)-9-(1,2-diphenylethenyl)carbazole

N-Phenylbenzaldimine (1.35 g, 0.0075 mol) and 9-benzylcarbazole (1.29 g, 0.0077 mol) were heated at 75° C. for 30 min in Na/DMF (see above). Based on reversed-phase HPLC results and a calibration curve the reaction reaches a plateau value after 15 min. Aqueous work-up as above and recrystallization of the precipitate from methanol gave needles mp 160-2° C. (58%).

EXAMPLE 23

(E)-N-Ethyl-N-phenyl-1,2-diphenyletheneamine

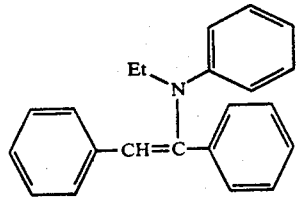

N-Benzyl-N-ethylaniline (2.11 g, 0.010 mol) and N-phenylbenzaldimine (2.00 g, 0.012 mol) were heated for 1 hr at 75° C. in dimethylformamide 50 mL and potassium tert-butoxide (5.6 g, 0.05 mol). Aqueous work-up as above, extraction with diethyl ether, and chromatography using 50 g of silica-60 with petroleum ether/benzene 8:2 (only 200 ml of solvent is needed). After evaporation of the solvent the oil was analyzed and then characterized further by hydrolysis (see below). MS [m/e (70 eV, % of base peak)] C$_{22}$H$_{21}$N 299 (M$^+$·, 39.7), 132 (M$^+$·—Ph$_2$CH·, 65.6), 104 (PhNCH$^+$, 58.4), 91 (C$_7$H$_7^+$, 100); HRMS (m/z) for C$_{14}$H$_{12}$O (M$^+$·) calcd. 299.167 found 299.168. $^1$H NMR (200 MHz, CDCl$_3$) δ (assignment): 1.25 (t, 3 H, J=4.8 Hz, methyl), 3.55 (q, 2 H,—NCH$_2$CH$_3$), 6.67-6.81 (m, 3 H, aromatic), 6.75 (s, 1 H, =CHPh), 7.11-7.54 (m, 12 H, aromatic). FTIR (CDCl$_3$): 3083, 3063, 3028, 2975, 2935, 2873, 1598, 1574, 1500, 1497, 1462, 1448, 1392, 1340, 1318 cm$^{-1}$.

EXAMPLE 24

Hydrolysis of (E)-N-ethyl-N-phenyl-1,2-diphenyletheneamine to Deoxybenzoin

The enamine was refluxed in tetrahydrofuran 30 mL and 1.9N sulfuric acid 3.0 mL for 1 hr. The solution was then treated with solid bicarbonate and the solvents were evaporated under reduced pressure. The residual oil was dissolved in diethyl ether and extracted with 1.9N H$_2$SO$_4$ 2×10 mL, washed with water 10 mL, aqueous bicarbonate 10 mL, and water 10 mL. The organic phase was filtered through sodium sulfate and the solvent was evaporated under reduced pressure. The residual oil was dissolved in boiling petroleum ether 30°-60° C. and cooled. This procedure deposited 1,2-diphenylethanone 1.2 g (61% based on the N-ethyl-N-phenylbenzylamine) mp 54-6° C.

EXAMPLE 25

(E),(E)-1,1'-[1,4-phenylene]bis-[2-phenyl-1-(diphenylamino)ethylene]

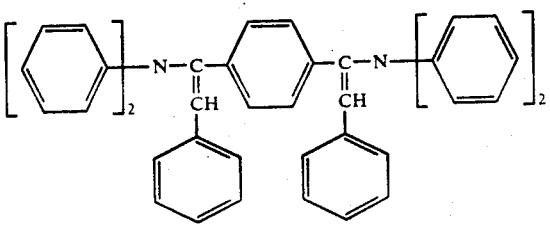

N-phenylbenzaldimine (1.81 g, 0.01 mol) and N,N,N',N'-tetraphenyl-a,a'-(1.4-xylenediyl)diamine (2.20 g, 0.005 mol) were reacted in potassium tert-butoxide (5.6 g, 0.05 mol) and dimethylformamide 50 ml at 75° C. for approximately 1 hr. Aqueous work-up precipitated the title compound which was recrystallized from acetone. It was purified by column chromatography using petroleum ether/benzene 98:2 as eluent. The yellow compound melts at 265-8° C. from acetone. $^1$H NMR (200 MHz, CDCl$_3$) δ (assignment): 6.68 (s, 2 H, =CHPh), 6.77-6.86 (m, 4 H, aromatic), 7.01-7.36 (m, 26 H, aromatic), 7.49 (s, 4 H, phenylene hydrogens). MS [m/e (70 eV, % of base peak)] 616 (M$^+$·, 62.9), 615 (M$^+$·—H·, 91.1), 449 (M$^+$·—Ph$_2$CH·, 50), 448 (M$^+$·—Ph$_2$N$^+$, 100), 282 (PhNC(C$_6$H$_4$)CNPh$^+$·, 55.5), 280 (PhCHC)C$_6$H$_4$)CCHPh$^+$·, 43.5). $^1$HNMR(200 MHz, CDCl$_3$) δ(assignment: 6.68 (s, 2H=CHPh), 7.01-7.36 (m 2 H), 7.19 (s, 4 H, phenylene). FTIR (CDCl$_3$) ν: 3066, 3035, 1590, 1492, 1447(w), 1408(w), 1353, 1327, 1310, 1293, 1277, 1230, 1219(w) cm$^{-1}$.

EXAMPLE 26

1,1'-(1,4-Phenylene)bis[2-phenylethanone

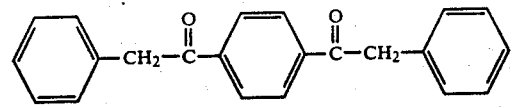

Chromotographed (E),(E)-1,1'-[1,4-phenylene]bis[2-phenyl-1-(diphenylamino)ethylene] (1.0 g, 0.0016 mol) was refluxed in a solution of THF (30 mL) and aqueous HCl (1.2M, 3.0 mL), for 1.25 h. The solution was worked-up as for the preparation of 1,2-diphenylethanone. Chromatography on silica (30 g) eluting with petroleum ether/benzene 3:2 removed from diketone. After solvent evaporation of the combined fractions and recrystallization of the residue from benzene/methanol gave small plates mp 171-3° C. (85%). FTIR (CDCl$_3$) ν: 3089, 3066, 3033, 2900, 1692(C=O), 1676, 1568, 1492, 1454, 1404, 1325, 1309, 1272, 1217, 1202 cm$^{-1}$. $^1$H NMR (200 MHz, CDCl$_3$) δ: 4.30 (s, 4 H, —CH$_2$Ph), 7.24-7.37 (m, 10 H, ending phenyls), 8.06 (s, 4 H, phenylene). MS [m/e (70 eV, % of base peak)] C$_{22}$H$_{18}$O$_2$ 314 (M$^+$·, 0.8), 223 (M$^+$·—PhCH$_2$·, 100), 104 (C$_6$H$_4$CO$^+$, 42.9), 91 (C$_7$H$_7^+$, 29).

In this specification aromatic ethers is to be understood to mean aryl, arylmethyl ethers; and aromatic tertiary amines is to be understood to mean diaryl, arylmethyl tertiary amines.

We claim:

1. An enamine of formula (V):

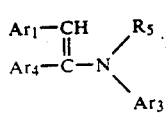
(V)

wherein $Ar_1$, $Ar_3$ and $Ar_4$ are each aromatic radicals independently senamine of formula (V):

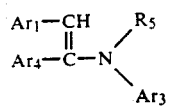
(V)

wherein $Ar_1$, $Ar_3$ and $Ar_4$ are each aromatic radicals independently selected from:

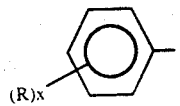

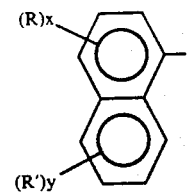

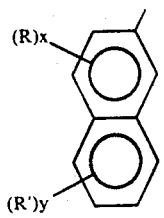

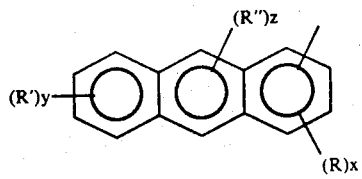

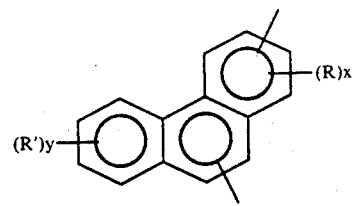

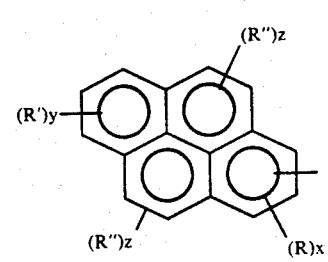

x and y are integers independently selected from 0, 1, 2 or 3 and z is an integer independently selected from 0, 1 or 2 and R, R' and R" are each independently selected from halogen atoms selected from F, Cl and Br; alkyl of 1 to 6 carbon atoms, alkenyl of 2 to 6 carbon atoms; aryl of 6 to 12 carbon atoms; aralkyl of 7 to 18 carbon atoms, aralkenyl of 8 to 18 carbon atoms, alkoxy of 1 to 6 carbon atoms, thioalkoxy of 1 to 6 carbon atoms; aryloxy of 6 to 12 carbon atoms and thioaryloxy of 6 to 12 carbon atoms, and $R_5$ is alkyl of 1 to 8 carbon atoms or a radical $Ar_6$, wherein $Ar_6$ is an aromatic radical as defined for $Ar_1$, $Ar_3$ and $Ar_4$ above.

2. An enamine according to claim 1, wherein $Ar_1$ and $Ar_4$ are the same and $R_5$ is said radical $Ar_6$.

* * * * *

UNITED STATES PATENT AND TRADEMARK OFFICE
CERTIFICATE OF CORRECTION

PATENT NO.   : 5,011,998

DATED        : April 30, 1991

INVENTOR(S)  : Allan S. Hay et al

It is certified that error appears in the above-identified patent and that said Letters Patent is hereby corrected as shown below:

At column 1, in Scheme (I), at line 25, insert an arrow ... —— ... between "$H_3C_2$-Ar" and "Ar-CH=CH-Ar" ".

At column 4, line 5, delete " 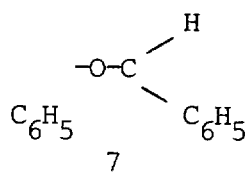 "   and insert therefor

... 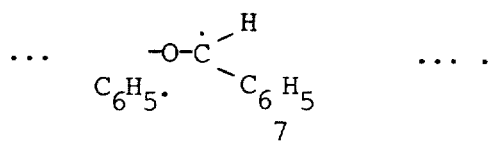 ... .

At column 4, line 15, delete "radial" and insert therefor ... radical ... .

At column 4, lines 30 to 45, delete the reaction scheme

UNITED STATES PATENT AND TRADEMARK OFFICE
CERTIFICATE OF CORRECTION

PATENT NO. : 5,011,998

DATED : April 30, 1991

INVENTOR(S) : Allan S. Hay et al

It is certified that error appears in the above-identified patent and that said Letters Patent is hereby corrected as shown below:

"Scheme 4

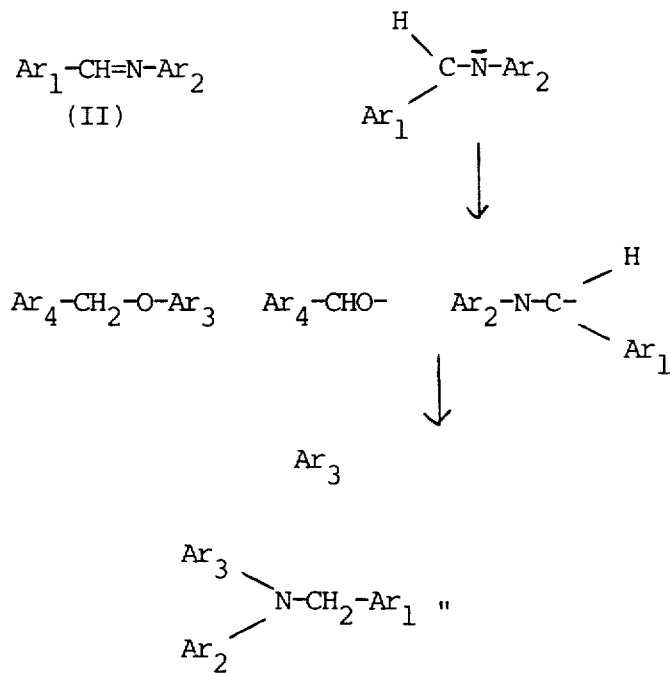

and insert therefor ...

UNITED STATES PATENT AND TRADEMARK OFFICE
CERTIFICATE OF CORRECTION

PATENT NO. : 5,011,998

DATED : April 30, 1991

INVENTOR(S) : Allan S. Hay et al

It is certified that error appears in the above-identified patent and that said Letters Patent is hereby corrected as shown below:

Scheme 4

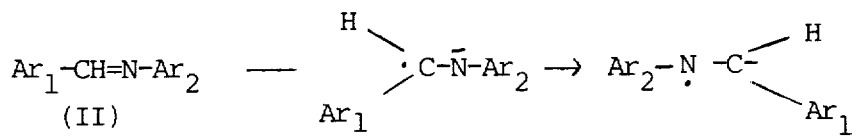

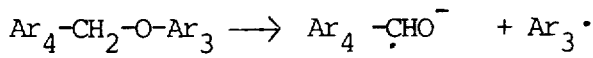

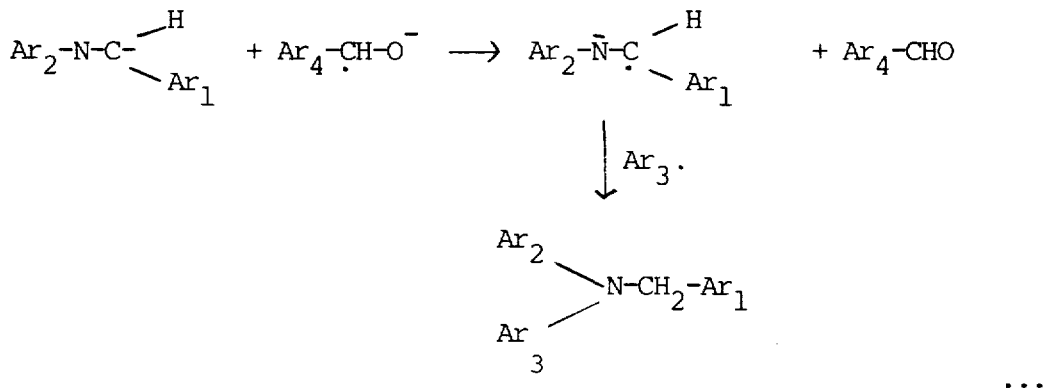

Col. 7 and 8 delete "Ar-C-C-Ar" and insert --Ar-C≡C-Ar--.

At column 9, line 35, in the structural formula delete "AR$_{10}$" and insert therefor ... Ar$_{10}$ ... .

At column 9, line 61, after ... sodium/ ... delete "-".

UNITED STATES PATENT AND TRADEMARK OFFICE
CERTIFICATE OF CORRECTION

PATENT NO. : 5,011,998

DATED : April 30, 1991

INVENTOR(S) : Allan S Hay et al

It is certified that error appears in the above-identified patent and that said Letters Patent is hereby corrected as shown below:

At column 13, line 3, change "dimethylethyl" to ... Dimethylethyl ... .

At column 13, line 39, change "naphthyl" to ... Naphthyl ... .

At column 15, line 7, change "methylphenyl" to ... Methylphenyl ... .

At column 15, line 47, change "methylphenyl" to ... Methylphenyl ... .

At column 23, delete lines 20 to 30 reading "wherein $Ar_1$, $Ar_3$ and $Ar_4$ are each aromatic radicals independently senamine of formula (V):

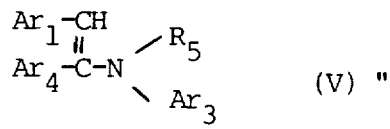

(V) "

Signed and Sealed this

Thirtieth Day of March, 1993

*Attest:*

STEPHEN G. KUNIN

*Attesting Officer*   *Acting Commissioner of Patents and Trademarks*